US010224035B1

(12) United States Patent
Koenig et al.

(10) Patent No.: US 10,224,035 B1
(45) Date of Patent: Mar. 5, 2019

(54) VOICE SEARCH ASSISTANT

(71) Applicants: Eric Koenig, Huntington, NY (US); David Borish, New York, NY (US); Jonathan Khoo, Fremont, CA (US)

(72) Inventors: Eric Koenig, Huntington, NY (US); David Borish, New York, NY (US); Jonathan Khoo, Fremont, CA (US)

(73) Assignee: PRIMO LLC, New York, NY (US)

( * ) Notice: Subject to any disclaimer, the term of this patent is extended or adjusted under 35 U.S.C. 154(b) by 0 days.

(21) Appl. No.: 16/120,357

(22) Filed: Sep. 3, 2018

(51) Int. Cl.
*G10L 15/26* (2006.01)
*G10L 15/22* (2006.01)
*G06T 11/60* (2006.01)
*G10L 15/30* (2013.01)
*A61B 5/0205* (2006.01)
*G06N 99/00* (2019.01)
*G06F 17/30* (2006.01)
*G10L 15/18* (2013.01)
*G10L 15/08* (2006.01)
*A61B 5/00* (2006.01)
*A61B 5/021* (2006.01)
*A61B 5/024* (2006.01)
*A61B 5/0402* (2006.01)
*A61B 5/145* (2006.01)

(52) U.S. Cl.
CPC .......... *G10L 15/22* (2013.01); *A61B 5/02055* (2013.01); *G06F 17/30864* (2013.01); *G06N 99/005* (2013.01); *G06T 11/60* (2013.01); *G10L 15/1815* (2013.01); *G10L 15/30* (2013.01); *A61B 5/0042* (2013.01); *A61B 5/021* (2013.01); *A61B 5/024* (2013.01); *A61B 5/0402* (2013.01); *A61B 5/14532* (2013.01); *A61B 5/14542* (2013.01); *A61B 2503/12* (2013.01); *G10L 2015/088* (2013.01); *G10L 2015/223* (2013.01)

(58) Field of Classification Search
USPC ........................................ 704/1–10, 230–277
See application file for complete search history.

(56) References Cited

U.S. PATENT DOCUMENTS

| 6,275,806 B1 * | 8/2001 | Pertrushin | G10L 17/26 704/270 |
| 6,651,042 B1 * | 11/2003 | Field | H04M 1/6505 379/100.05 |
| 8,417,530 B1 * | 4/2013 | Hayes | G06F 17/30026 704/1 |

(Continued)

*Primary Examiner* — Huyen X Vo
(74) *Attorney, Agent, or Firm* — Georgiy L. Khayet

(57) ABSTRACT

Systems and methods for assisting voice searches are provided. An example method commences with receiving a voice query from a user and transmitting the voice query to a plurality of natural language processing systems. The method may continue with receiving a plurality of search parameter sets generated by the plurality of natural language processing systems based on the voice query. The method may further include transmitting at least one of the plurality of search parameter sets to a plurality of information search systems. The method may continue with receiving a plurality of responses from the plurality of information search systems. The plurality of responses may be generated by the plurality of information search systems based on the at least one of the plurality of search parameter sets. The method may conclude with providing at least one response of the plurality of responses to the user.

17 Claims, 12 Drawing Sheets

(56) References Cited

U.S. PATENT DOCUMENTS

| | | | |
|---|---|---|---|
| 9,070,366 B1* | 6/2015 | Mathias | G06F 17/279 |
| 9,761,249 B2* | 9/2017 | Deleeuw | G10L 25/63 |
| 2008/0005068 A1* | 1/2008 | Dumais | G06F 17/30528 |
| 2015/0213123 A1* | 7/2015 | Peters | G06F 17/30032 |
| | | | 707/728 |
| 2017/0140759 A1* | 5/2017 | Kumar | G10L 15/32 |
| 2018/0293983 A1* | 10/2018 | Choi | G10L 15/22 |

* cited by examiner

VOICE SEARCH ASSISTANT

TECHNICAL FIELD

The present disclosure relates generally to data processing and, more particularly, to voice-enabled digital assistants.

BACKGROUND

The use of voice searches and voice-enabled devices is rapidly expanding. Currently, many network-connected digital devices, such as smartphones, smart watches, smart in-home appliances, and so forth use voice-enabled assistants. A voice-enabled assistant may include a software agent that uses voice recognition technology to perform tasks or services for a user. A conventional voice-enabled assistant agent running on a digital device can receive a voice query from the user, convert the voice query into text, and perform a command based on the text (for example, perform an action on the digital device or facilitate a search on the Internet).

A voice query typically entails providing text to a third-party voice recognition system that analyzes the text and conducts the search based on the analysis of the text. The voice-enabled assistant receives results from the third-party voice recognition system and provides the results to the user. However, the selected third-party voice recognition system may not be the best third-party voice recognition system in general or not the optimal fit for a specific query. Thus, existing solutions may lack the ability to automatically select an optimal third-party voice recognition system.

Furthermore, the third-party search engines can perform semantic analysis of the text; however, various parameters associated with the voice query can be left out of consideration. Such parameters can include emotions expressed by the user when pronouncing the voice query, urgency of the request, environmental sounds present in the voice query, an emphasis made by the user when uttering a phrase, and so forth. In the absence of an analysis of the whole range of parameters of the voice query, the search results may be incomplete or insufficiently relevant to the voice query.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are computer-implemented systems and methods for assisting voice searches. In some example embodiments, a system for assisting voice searches may include a processor and a database communicatively coupled to the processor and storing instructions executable by the processor. The processor may be configured to receive a voice query from a user and transmit the voice query to a plurality of natural language processing systems. The processor may be further configured to receive a plurality of search parameter sets from the plurality of natural language processing systems. The plurality of search parameter sets may be generated by the plurality of natural language processing systems based on the voice query. The processor may be configured to transmit at least one of the plurality of search parameter sets to a plurality of information search systems. The processor may be further configured to receive a plurality of responses from the plurality of information search systems. The plurality of responses may be generated by the plurality of information search systems based on the at least one of the plurality of search parameter sets. The processor may be further configured to provide at least one response of the plurality of responses to the user.

In some example embodiments, a method for assisting voice searches may commence with receiving a voice query from a user and transmitting the voice query to a plurality of natural language processing systems. The method may continue with receiving a plurality of search parameter sets from the plurality of natural language processing systems. The plurality of search parameter sets may be generated by the plurality of natural language processing systems based on the voice query. The method may further include transmitting at least one of the plurality of search parameter sets to a plurality of information search systems. The method may then continue with receiving a plurality of responses from the plurality of information search systems. The plurality of responses may be generated by the plurality of information search systems based on the at least one of the plurality of search parameter sets. The method may conclude with providing at least one response of the plurality of responses to the user.

Additional objects, advantages, and novel features will be set forth in part in the detailed description section of this disclosure, which follows, and in part will become apparent to those skilled in the art upon examination of this specification and the accompanying drawings or may be learned by production or operation of the example embodiments. The objects and advantages of the concepts may be realized and attained by means of the methodologies, instrumentalities, and combinations particularly pointed out in the appended claims.

BRIEF DESCRIPTION OF THE DRAWINGS

Embodiments are illustrated by way of example and not limitation in the figures of the accompanying drawings, in which like references indicate similar elements and, in which.

DETAILED DESCRIPTION

Figure 1:
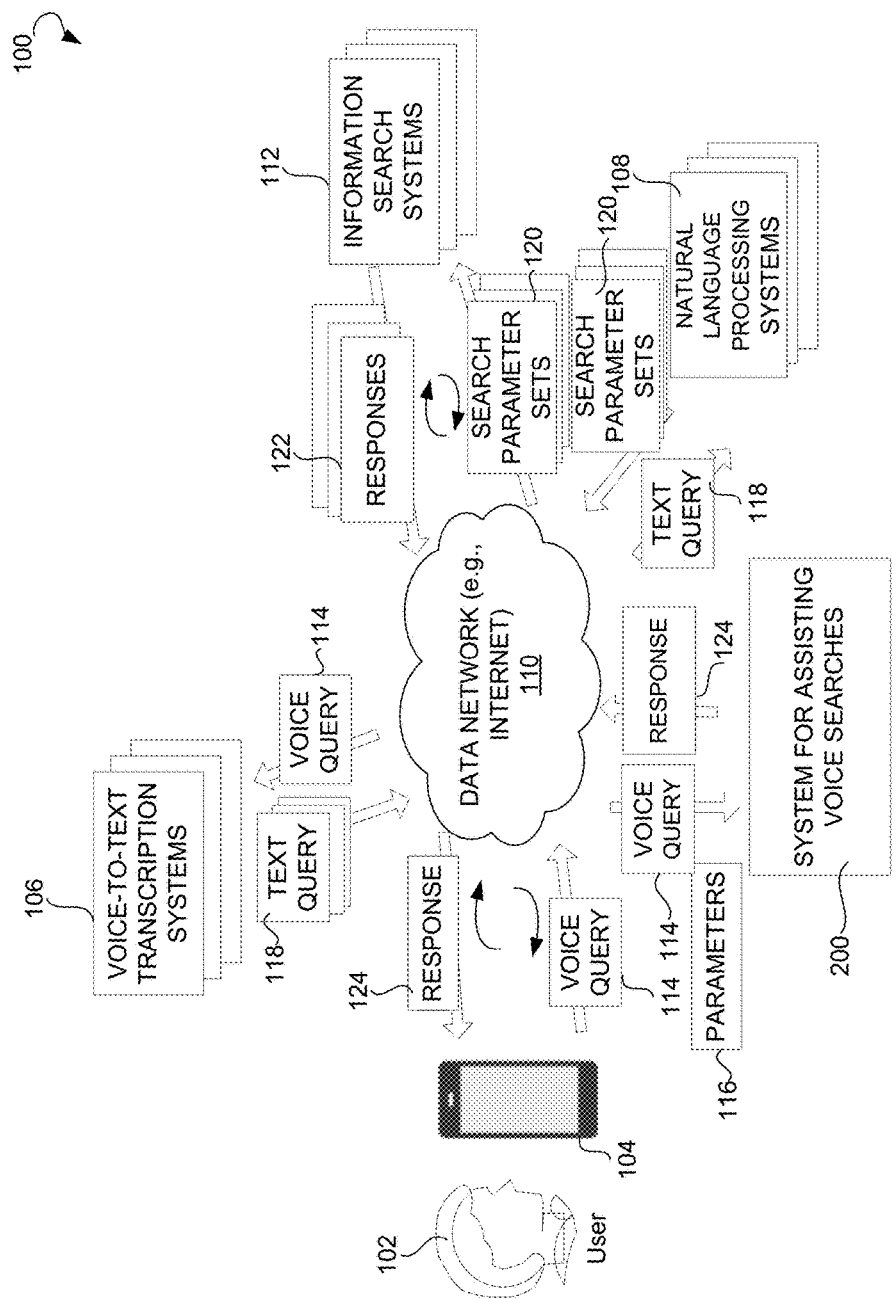
FIG. 1 illustrates an environment within which systems and methods for assisting voice searches can be implemented, in accordance with some embodiments.

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed. The following detailed description is, therefore, not to be taken in a limiting sense, and the scope is defined by the appended claims and their equivalents.

The present disclosure provides methods and systems for assisting voice searches. The systems for assisting voice searches of the present disclosure may be implemented in a form of a voice search assistant installed on a digital device of a user, such as a smartphone, a tablet computer, a smart in-home appliance, and the like. The user may provide a voice query to the system for assisting voice searches running on the digital device. The system may receive the voice query and provide the voice query to a plurality of voice-to-text transcription systems. The system may be in communication with a plurality of third-party voice-to-text transcription systems, such as, Amazon Transcribe™ from Amazon, Dragon Dictation™ from Nuance Communications, Verbal Ink™, Athreon™, Descript™, and so forth. Each of the voice-to-text transcription systems may convert the voice query into a text query and provide the text query to the system of this disclosure. The system may score the text queries received from the plurality of voice-to-text transcription systems, for example, based on the reliability of each of the plurality of voice-to-text transcription systems, and select a text query having the highest score.

Furthermore, the system may be in communication with a plurality of third-party natural language processing systems. The natural language processing systems may include Amazon Comprehend™ from Amazon, Google Cloud Natural Language API from Google, Microsoft Azure™ from Microsoft, Language Understanding Intelligent Service (LUIS™) from Microsoft, Watson Natural Language Understanding™ from IBM, and so forth. The system may provide the selected text query to each of the plurality of natural language processing systems. Alternatively, the system may forward the voice query to the plurality of natural language processing systems without performing the text recognition, and each of the plurality of natural language processing may convert the received voice query into the text query.

Each of the plurality of natural language processing systems may analyze the text query to determine a search parameter set. The search parameter set may include search criteria, such as key words, terms, phrases, dates, locations, events, brand names, context, syntax, and the like. The system may receive a plurality of search parameter sets from the plurality of natural language processing systems. The system may score the plurality of search parameter sets, for example, based on the reliability of each of the natural language processing systems, and select the search parameter set having the highest score.

The system may further be in communication with a plurality of information search systems. The information search systems may include a plurality of datasets, e.g., databases, and a plurality of third-party virtual search assistants. The third-party virtual search assistants may include intelligent personal assistants, web search engines, and the like, such as Google Assistant® from Google, Alexa® from Amazon, Siri® from Apple, Cortana® from Microsoft, Bixby® from Samsung, and so forth. The system of the present disclosure may forward the selected search parameter set to a plurality of information search systems.

The system may also analyze the voice query to derive parameters of the voice query. The parameters may be determined by analyzing sound data of the user voice and environmental sound data, for example, a tone, a tempo, an inflection, a sentiment, an urgency, an emphasis, an environmental parameter, and the like. The parameters, e.g., a keyword, a term, a phrase, may be further determined by semantic analysis of the voice query. Additionally, the parameters may be determined by analyzing video data captured by a camera of the digital device, such as a gesture, a body motion, a body language, a visual cue, a facial expression, and so forth. The parameters may further include ambient data, user demographics, a user location, historical data, and so forth. Additionally, specific search intent algorithms may be used to analyze the voice query and determine a desire, an intent, a purpose of the voice query, and the like.

Each information search system may process the search parameter set and provide a response to the system of the present disclosure. The system may receive a plurality of responses from the information search systems and use machine learning and Artificial Intelligence (AI) technologies to process the responses. Specifically, the system may score each response based on predetermined scoring criteria. The scoring may be based on the parameters of the voice query determined by the system and historical data associated with each of the information search systems. The historical data associated with the information search systems may include data related to the likelihood of success in providing relevant responses by each of the information search systems to previous voice queries.

In other words, the historical data may be indicative of correctness of each information search system for a specific query. For example, according to the historical data, a first information search system may process specific types of queries in a more efficient way than other information search systems; in particular, the first information search system may provide the best (based on some predetermined criteria) response 60% of the time for this type of query. In another example embodiment, specific tones of the voice queries may be processed in the most efficient way by a second information search system. The predetermined scoring criteria may include environmental sensor data, user demographics, key word assessment based on a user location, historical data indicative of general reliability of the plurality of the information search systems, and historical data indicative of a reliability of the plurality of the information search systems with respect to the voice query.

Alternatively, the system may forward the voice query to the plurality of information search systems without performing the text recognition and determining the search parameter sets, and each of the plurality of information search may convert the received voice query into the text query and generate the search parameter set associated with the text query.

After scoring the responses, the system may rank the responses based on a score determined for each response. The system may provide a response prioritized in the list of ranked responses to the digital device of the user as an answer to the voice query. Alternatively, the system can provide the list of ranked responses to the user so that the user can decide which one to use.

The system may also assign weights to each response obtained from the information search systems. The weights can be assigned based on the scoring. Upon assigning the weights, the system can combine all responses received from the information search systems into an aggregated response based on the weight of each of the responses. In this case, the response provided to the user may be in the form of an aggregated response.

FIG. 1 illustrates an environment 100 within which systems and methods for assisting voice searches can be implemented, in accordance with some embodiments. The environment 100 may include a user 102, a user device 104, a system 200 for assisting voice searches (also referred to as a system 200), voice-to-text transcription systems 106, natural language processing systems 108, information search systems 112, and a data network 110 (e.g., the Internet or a computing cloud). The user device 104, the system 200, the voice-to-text transcription systems 106, the natural language processing systems 108, and the information search systems 112 may be connected via the data network 110.

The user 102 may be associated with the user device 104. The user device 104 may include a personal computer (PC), a laptop, a smartphone, a tablet PC, a television set, a smartphone, an Internet phone, a netbook, a network appliance, a speaker unit, a digital device, and so forth.

The data network 110 may include a computing cloud, the Internet, or any other network capable of communicating data between devices. Suitable networks may include or interface with any one or more of, for instance, a local intranet, a corporate data network, a data center network, a home data network, a Personal Area Network, a Local Area Network (LAN), a Wide Area Network (WAN), a Metropolitan Area Network, a virtual private network, a storage area network, a frame relay connection, an Advanced Intelligent Network connection, a synchronous optical network connection, a digital T1, T3, E1 or E3 line, Digital Data Service connection, Digital Subscriber Line connection, an Ethernet connection, an Integrated Services Digital Network line, a dial-up port such as a V.90, V.34 or V.34bis analog modem connection, a cable modem, an Asynchronous Transfer Mode connection, or a Fiber Distributed Data Interface or Copper Distributed Data Interface connection. Furthermore, communications may also include links to any of a variety of wireless networks, including Wireless Application Protocol, General Packet Radio Service, Global System for Mobile Communication, Code Division Multiple Access or Time Division Multiple Access, cellular phone networks, Global Positioning System, cellular digital packet data, Research in Motion, Limited duplex paging network, Bluetooth radio, or an IEEE 802.11-based radio frequency network. The data network can further include or interface with any one or more of a Recommended Standard 232 (RS-232) serial connection, an IEEE-1394 (FireWire) connection, a Fiber Channel connection, an IrDA (infrared) port, a Small Computer Systems Interface connection, a Universal Serial Bus (USB) connection or other wired or wireless, digital or analog interface or connection, mesh or Digi® networking.

The system 200 may be running on the user device 104. In an example embodiment, the system 200 may be installed on the user device 104 in a form of a voice search assistant. The user 102 may provide a voice query 114 to the system 200 using the user device 104. The system 200 may receive the voice query 114 and determine parameters 116 of the voice query 114. The system 200 may further send the voice 114 query to the voice-to-text transcription systems 106. Each of the voice-to-text transcription systems 106 may convert the voice query 114 into text queries 118 and provide the text queries 118 to the system 200. The system 200 may select at least one text query 118 and send the selected text query 118 to the natural language processing systems 108. Each of the natural language processing systems 108 may process the text query 118, generate search parameters sets 120, and provide the search parameters sets 120 to the system 200. The system 200 may select at least one search parameters set 120 and send the selected at least one search parameters set 120 to the information search systems 112. The information search systems 112 may perform a search based on the at least one search parameters set 120 and generate responses 122. The system may receive the responses 122 from all information search systems 106, process the responses 122 based on at least the parameters 116, select at least one response 124 from the responses 122, and provide the selected response 124 to the user device 104 as an answer to the voice query 114.

Figure 2:
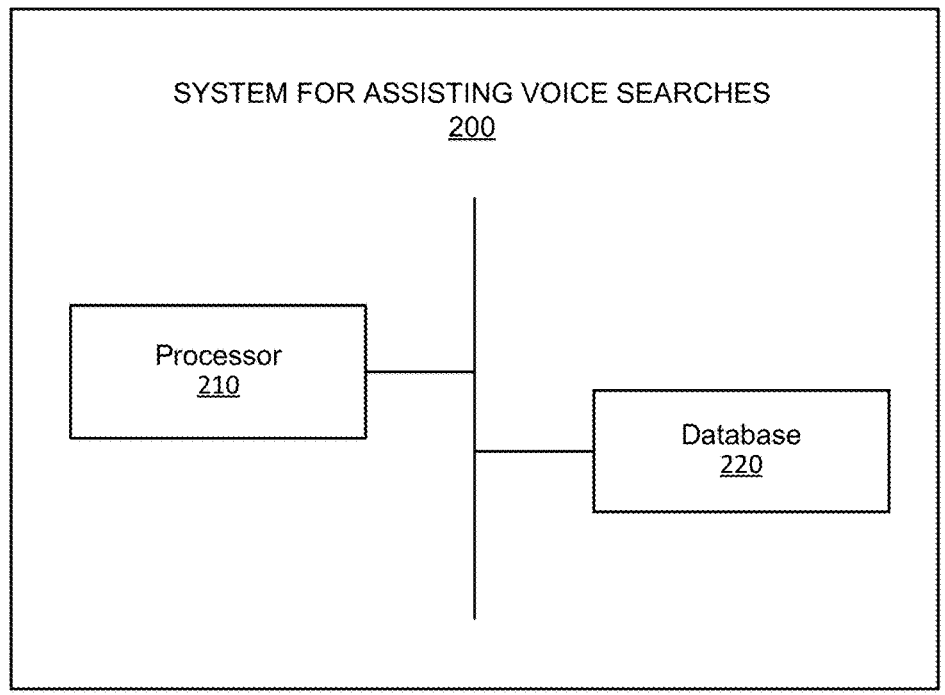
FIG. 2 is a block diagram showing various modules of a system for assisting voice searches, in accordance with certain embodiments.

FIG. 2 is a block diagram showing various modules of a system 200 for assisting voice searches, in accordance with certain embodiments. The system 200 may include a processor 210 and a database 220. The database 220 may include computer-readable instructions for execution by the processor 210. The processor 210 may include a programmable processor, such as a microcontroller, central processing unit (CPU), and so forth. In other embodiments, the processor 210 may include an application-specific integrated circuit or programmable logic array, such as a field programmable gate array, designed to implement the functions performed by the system 200. In various embodiments, the system 200 may be installed on a user device or may be provided as a cloud service residing in a cloud storage.

The processor 210 may be operable to receive a voice query from a user. The processor 210 may be further operable to analyze parameters associated with the voice query. In an example embodiment, the parameters may include at least one of the following: a tone, a tempo, an inflection, a sentiment, an urgency, an emphasis, a keyword, a term, a phrase, a visual cue, a gesture, a body motion, a body language, a desire, an intent, a facial expression, an environmental parameter, ambient data, user demographics, a user location, historical data, time data, such as time of a day, and so forth. The analysis of the parameters of the voice query may be performed using AI and machine learning techniques. The sentiment, inflection, tone, urgency, desire, and intent may be determined using search intent algorithms. The visual cue may be obtained via a camera and include a background, landmark, and the like.

The search intent algorithms may be machine learning and AI algorithms used to determine parameters of the voice query. The search intent algorithms may be used to determine one or more of the following parameters: an inflection, intent of the user, desire of the user when uttering a voice query, purpose of the voice query, priority set by the user for some phrases, the most important word, phrase, or question of the query, a sequence of the questions, the user goal of the query, and any other metrics that may be calculated for the user query and further utilized to determine relevant search results.

The processor 210 may store the determined parameters to the database 220. The parameters associated with the voice queries of a plurality of users may be collected and stored in the database 220 and may be used later upon processing further voice queries.

The processor 210 may be in communication with a plurality of natural language processing systems. The communication between the processor 210 and each of the plurality of natural language processing systems may include a secure communication channel. The processor 210 may be further configured to transmit the voice query to a plurality of natural language processing systems.

In an example embodiment, the transmission of the voice query to the plurality of natural language processing systems includes first transmitting the voice query to a plurality of voice-to-text transcription systems. Specifically, the processor 210 may be in communication with the plurality of voice-to-text transcription systems. The communication between the processor 210 and each of the plurality of voice-to-text transcription systems may include a secure communication channel. In response to the voice query, the processor 210 may receive a plurality of text queries from the plurality of voice-to-text transcription systems. In an example embodiment, the processor 210 may score each of the plurality of text queries based on the predetermined scoring criteria and select at least one text query having the highest score. The processor 210 may send the selected at least one text query to the plurality of natural language processing systems.

The processor 210 may be further configured to receive a plurality of search parameter sets from the plurality of natural language processing systems. The plurality of search parameter sets may be generated by the plurality of natural language processing systems based on the voice query. In an example embodiment, the plurality of natural language processing systems may process the voice query by processing the at least one text query received from the system 200. The plurality of search parameter sets can include one or more of the following: key words, terms, phrases, dates, locations, events, brand names, and so forth.

The processor 210 may be further configured to score each of the plurality of search parameter sets based on predetermined scoring criteria and rank the plurality of search parameter sets based on the score to select at least one search parameter set having a highest rank.

The processor 210 may be in communication with a plurality of information search systems. The communication between the processor 210 and each of the plurality of information search systems may include a secure communication channel. Each of the information search systems may include a programming interface. The plurality of information search systems can include at least one of the following: a plurality of information datasets and a plurality of virtual search assistants. The plurality of virtual search assistants may include Google Assistant® from Google, Alexa® from Amazon, Siri® from Apple, Cortana® from Microsoft, Bixby® from Samsung, and so forth. The processor 210 may be configured to transmit at least one search parameters set selected from the plurality of search parameter sets to the plurality of information search systems. Specifically, the processor 210 may transmit the at least one search parameter set to each of the plurality of information search systems using the corresponding programming interface (e.g. API) of each of the plurality of information search systems.

Additionally, the processor 210 may transmit, along with the at least one of the plurality of search parameter sets, a data packet to the plurality of information search systems. The data packet may contain additional data, such as flags or metadata associated with parameters of the voice query determined by the processor 210. The data packet containing additional data may be sent together with the voice query or separate from the voice query.

Each of plurality of information search systems may process the received at least one of the plurality of search parameter sets and, optionally, metadata and generate a response to the voice query. The processor 210 may receive a plurality of responses from the plurality of information search systems. The processor 210 may score each of the plurality of responses based on predetermined scoring criteria. In an example embodiment, the predetermined scoring criteria may include at least one of the following: environmental sensor data, user demographics, key word assessment based on a user location, historical data indicative of general reliability of the plurality of the natural language processing systems, historical data indicative of reliability of the plurality of the information search systems with respect to the voice query, historical data indicative of general reliability of the plurality of the voice-to-text transcription systems, historical data indicative of general reliability of the plurality of the information search systems, and so forth.

The processor 210 may be configured to determine which response of the plurality of responses is to be presented to the user. Specifically, the processor 210 may score each of the plurality of responses based on the predetermined scoring criteria. Additionally, the processor 210 may score each of the plurality of responses based on the parameters associated with the voice query that are previously determined by the processor 210. The processor 210 may use weighting and ranking algorithms to rank the plurality of responses based on the scoring and select the at least one response. The selected at least one response may have a highest rank. The processor 210 may provide the selected at least one response to the user as an answer to the voice query.

In an example embodiment, the processor 210 may be further configured to assign weights to each of the plurality of responses based on the score. In this case, the processor 210 may combine the plurality of responses received from the plurality of information search systems, based on the assigned weights, into an aggregated response. The response provided to the user may be the aggregated response, i.e., a summation of the plurality of responses received from the plurality of information search systems according to the assigned weights. In a further example embodiment, the processor 210 may be configured to provide a list of ranked responses to the user based on the weights.

In an example embodiment, the processor 210 may convert the voice query into a text query without sending the voice query to the plurality of voice-to-text transcription systems. Upon conversion, the processor 210 may send the text query to the natural language processing systems for further processing.

In a further example embodiment, the processor 210 may transmit the voice query to the plurality of information search systems without conversion of the voice query into text query and generating search parameters sets first. In this case, the information search systems may convert the voice query into the text query and generate a search parameters set based on the text query. Additionally, the processor 210 may be configured to partition the voice query prior to transmission of the voice query to the plurality of the information search systems. In this case, each part of the voice query may be scored separately. Upon partitioning of the voice query, the processor 210 may choose specific information search systems to which the part of the voice query is to be sent. The parts of the voice query can be sent to all of the information search systems or to different information search systems. For example, the processor 210 may select a first information search system for processing one part of the voice query and select a second information search system for processing another part of the voice query. The processor 210 may select particular information search systems based on historical data associated with the information search systems or various predetermined criteria.

In an example embodiment, parallel processing techniques may be used for processing parts of the voice query. Specifically, the processor 210 may determine, based on the historical data, that the first information search system provides the best results for a specific type of the voice query. Therefore, if the part of the voice query has the parameters corresponding to the type of the voice query, the processor 210 may select the first information search system for processing the part. The responses received from the plurality of information search systems may include the responses to that specific part. The response provided to the user may include a combination of the responses to the separate parts of the voice query. Combination of the responses may be performed based on the scoring.

In a further example embodiment, the processor 210 may determine that more information is needed for the voice query. Based on the determination, the processor 210 may generate at least one follow-up question to clarify the voice query and provide the at least one follow-up question to the user.

In some example embodiments, the processor 210 may determine, based on the voice query, that the user requires help of at least one first responder. For example, the voice query may include specific key words, such as "blood," "accident," "injury," and the like. In another example, the voice of the user may be excessively emotional. Based on such determination, the processor 210 may send a request for help to the first responder. The first responders may include emergency responders, such as police officers, firefighters, paramedics, and the like. The request for help may further include a user location. In an example embodiment, the user location may be determined by location services associated with the user device, such as a global positioning system (GPS), when location services are enabled on the user device, or by using other location techniques. In a further example embodiment, the location data may be requested from the user device upon determining that the user requires help. The user location may be one of the environmental parameters determined based on the analysis of the voice query. Additionally, data associated with the user location, such as images of objects in proximity to the user or a video, may be captured by a camera of the user device. Based on the images and video, the processor 210 may find visual cues in the background and recognize some landmarks or other relevant information. Additionally, visual cues related to the user may be captured by the camera and analyzed by the processor 210, such as the type of the injury, appearance of the user, physical condition of the user, and so forth. The determined data may be provided to the first responder and may be helpful for locating the user, selecting emergency measures, or any other purposes.

In further example embodiments, the processor 210 may be configured to analyze the user query based on biosensory data received from one or more sensors and modify the at least one response based on the analysis. The biosensory data may include at least one of the following: a brain scan, a blood pressure, heart rate, body temperature, electrocardiogram, blood oxygenation level, blood sugar level, physical activity, and the like. The sensors may include biological sensors, physiological sensors, biofeedback sensors, brain imaging devices, or any other types of sensors associated with the user device or any other device associated with the user and in communication with the user device, such as a health monitoring device, a smartwatch, a fitness tracker, smart glasses, and the like. Additionally, the processor 210 may have access to medical data of the user collected beforehand and may use the medical data when analyzing the biosensory data. In an example embodiment, the biosensory data may be used to further analyze parameters of the voice query and determine a sentiment of the voice query.

In a further example embodiment, voice data associated with the plurality of users may be collected, analyzed, and further used for comparing with the voice data received from the user in a current voice query. The voice data collected from the plurality of users may be analyzed to determine the sentiment associated with the current voice query of the user. The sentiment of the current voice query may be determined by comparing the parameters of the current voice query with the parameters of the voice data collected from the plurality of users.

In another example embodiment, the user may select a subscription plan. Accordingly, to this example, if the user has a premium subscription plan, all available information search systems may be used for processing voice queries of the user. Fewer information search systems may be used for processing voice queries of a user that has a standard subscription plan.

In an example embodiment, the system 200 may be configured to provide a topic-specific service to users. For example, the system 200 may be associated with an enterprise and in communication with information search systems connected to topic-specific databases. A user, e.g., an employer or a client of the enterprise, may provide topic-specific voice queries to the system 200. The topic-specific voice queries may relate to services or activities of the enterprise, such as legal matters, treatment of specific diseases, industry-specific issues, and the like. The information search systems may be configured to provide responses to topic-specific voice queries based on data stored in topic-specific databases.

In an example embodiment, the environment captured by the camera of the user device and shown to the user can be augmented using augmented reality (AR) technology. Specifically, the processor 210 of the user device or a cloud in communication with the user device may select and add items to the environment shown via an AR application and display the augmented environment on an AR enabled device. The items may be selected based on the context associated with the recognized elements. In an example embodiment, the items shown to the user may be used for advertising and commerce purposes, and may include, for example, a link to a web site that sells a product, a link to a social media profile of a company that owns the product, a description of a product taken from a web site, a route to a shop, and the like. In an example embodiment, the AR environment may be shown to the user in combination with the response.

In some example embodiments, the system 200 can make proactive and elevated sponsored recommendations based on the context of the voice query (e.g., the location of the user) and/or based on the context of actions the user performed in the past (e.g., previous voice queries, interaction of the user with the user device, and so forth). Specifically, the processor 210 may be configured to rank the plurality of responses based on sponsored recommendations and/or suggestions related to context of the voice query and/or based on context of historical actions performed by the user. The sponsored recommendations may be obtained from third party advertisers unrelated to the search and may be based on predetermined parameters, such as a user profile, location, time of a day, atmospheric conditions, and so forth. Specifically, the sponsored recommendations can include sponsored search results, for example, advertisements paid for by a web site owner for displaying (or elevated in the search results) a web site in response to search queries based on the predetermined parameters. The sponsored results may be prioritized in search results over organic search results, i.e., search results that are most relevant to the voice query of the user.

In a further example embodiment, the recommendations and suggestions may be obtained from a shopping list/wish list associated with the user. For example, the recommendations and suggestions may be obtained from applications and various functionalities utilized by the user, such as notes applications, reminders applications, calendar applications, APIs from retail applications, and so forth. The data obtained from the applications may be used to direct the user to relevant retail locations. The user may be directed using a combination of verbal dialogues, onscreen prompts, and the like.

In some example embodiments, the textual data can be visualized through AR or virtual reality (VR) applications running on user devices such as a smartphone, goggles, helmets, glasses, or even contact lenses. The textual data can also be superimposed on traditional images or video as a hologram. In other words, the processor 210 may be configured to select and add, by an AR means, items to an environment to generate an augmented environment and show, by the AR means, the augmented environment to the user in combination with the at least one response.

Figure 3:
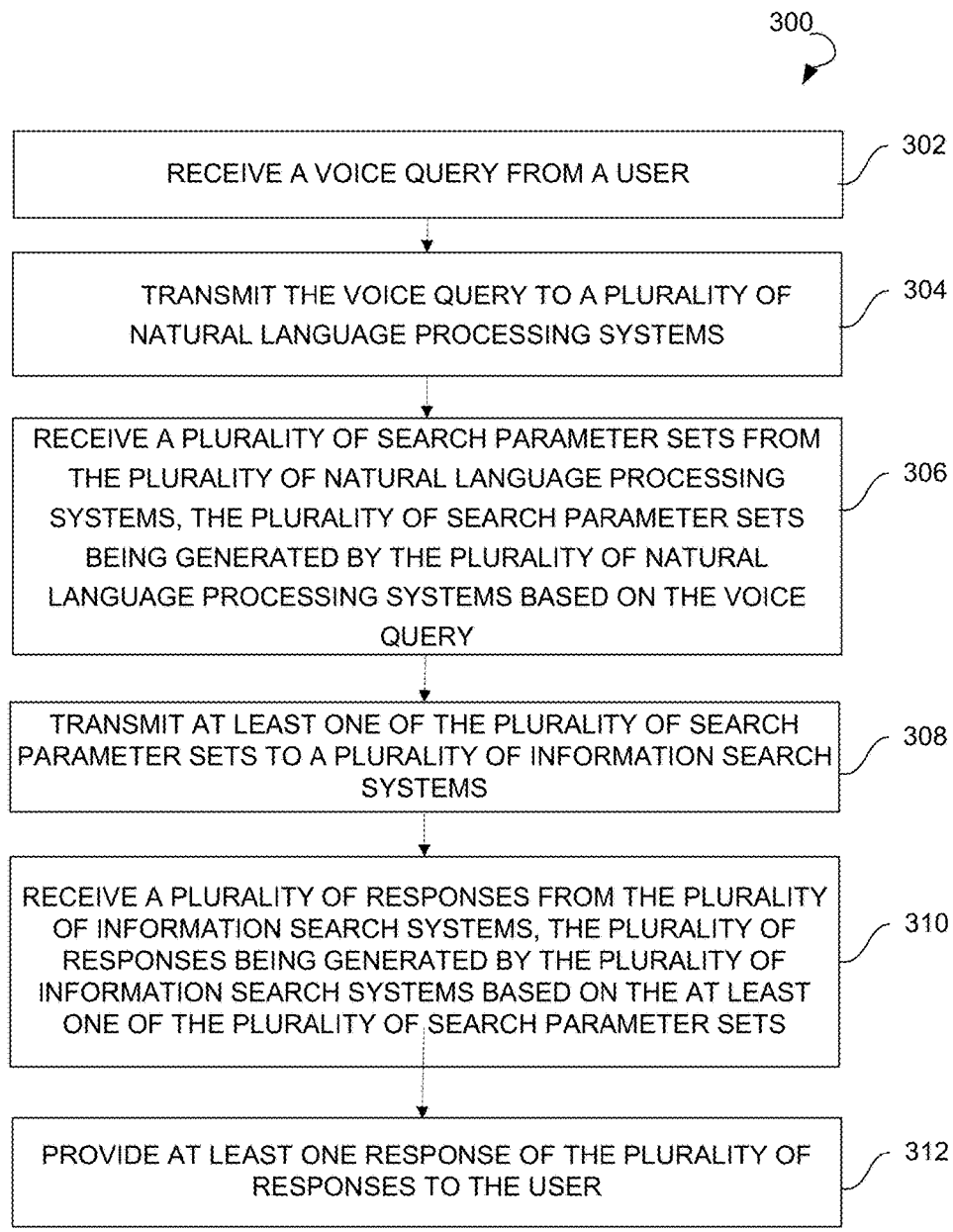
FIG. 3 is a flow chart illustrating a method for assisting voice searches, in accordance with some example embodiments.

FIG. 3 is a flow chart illustrating a method 300 for assisting voice searches, in accordance with some example embodiments. In some embodiments, the operations may be combined, performed in parallel, or performed in a different order. The method 300 may also include additional or fewer operations than those illustrated. The method 300 may be performed by processing logic that may comprise hardware (e.g., decision making logic, dedicated logic, programmable logic, and microcode), software (such as software run on a general-purpose computer system or a dedicated machine), or a combination of both.

The method 300 may commence with receiving, by a processor, a voice query from a user at operation 302. The voice query may be received using a user device associated with the user. The method 300 may optionally continue with analyzing, by the processor, parameters associated with the voice query. The parameters may include at least one of the following: a tone, tempo, inflection, sentiment, urgency, emphasis, keyword, term, phrase, visual cue, gesture, body motion, body language, desire, intent, facial expression, environmental parameter, ambient data, user demographics, user location, historical data, and so forth. The sentiment, the inflection, the tone, the urgency, the desire, and the intent may be determined using search intent algorithms. The visual cue may be obtained via a camera and may include a background, a landmark, and the like.

The method 300 may further optionally include transmitting the voice query to a plurality of voice-to-text transcription systems. Specifically, the voice query may be transmitted to the plurality of voice-to-text transcription systems via at least one programming interface of the plurality of voice-to-text transcription systems. The method 300 may further include receiving a plurality of text queries from the plurality of voice-to-text transcription systems. Each of the plurality of text queries may be scored based on the predetermined scoring criteria to select at least one text query having a highest score.

The method 300 may further include operation 304 at which the voice query is transmitted by the processor to a plurality of natural language processing systems. In an example embodiment, transmitting the voice query to the plurality of natural language processing systems includes transmitting the at least one text query selected from the plurality of text queries received from the plurality of voice-to-text transcription systems. Specifically, the voice query or the text query may be transmitted to the plurality of natural language processing systems via at least one programming interface of the plurality of natural language processing systems.

The method 300 may continue at operation 306 with receiving a plurality of search parameter sets from the plurality of natural language processing systems. The plurality of search parameter sets may be generated by the plurality of natural language processing systems based on the voice query. In an example embodiment, the generation of the plurality of search parameter sets is based on the text query received by the plurality of natural language processing systems from the processor.

In another example embodiment, each of the plurality of search parameter sets may be scored based on predetermined scoring criteria and ranked based on the score. Based on the ranking, at least one search parameter set having a highest rank, may be selected.

The method 300 may further include transmitting the at least one of the plurality of search parameter sets to a plurality of information search systems at operation 308. The method 300 may continue with operation 310, at which the processor may receive a plurality of responses from the plurality of information search systems. The plurality of responses may be generated by the plurality of information search systems based on the at least one of the plurality of search parameter sets. Optionally, the method 300 may further include scoring, by the processor, each of the plurality of responses based on predetermined scoring criteria. The predetermined scoring criteria may include at least one of the following: environmental sensor data, user demographics, key word assessment based on the user location, historical data indicative of general reliability of the plurality of the natural language processing systems, historical data indicative of reliability of the plurality of the information search systems with respect to the voice query, historical data indicative of general reliability of the plurality of the voice-to-text transcription systems, historical data indicative of general reliability of the plurality of the information search systems, and so forth. The method 300 may include assigning weights to each of the plurality of responses based on the scoring.

Optionally, the method 300 may include ranking the plurality of responses based on the score. The method 300 may then continue with providing at least one response selected based on the ranking to the user as an answer to the voice query at operation 312. In an example embodiment, the method 300 may include providing a list of ranked responses to the user. In a further example embodiment, the at least one response may include a combination of the plurality of responses received from the plurality of information search systems. The plurality of responses may be combined based on the assigned weights.

In a further example embodiment, the method 300 may include determining that more information is needed to clarify the voice query. Based on such determination, at least one follow-up question may be generated to clarify the voice query. The AI algorithms may determine that the responses received from the information search systems are incomplete or irrelevant and ask questions to better understand the voice query of the user. The questions may be made provided to the user using the user device or the speaker unit. The user may reply to the questions and the user voice of the reply may be sensed by the user device or the speaker unit.

Thereafter, the transcription of the user voice may be performed. The obtained text may be provided to the search intent algorithms for analysis to determine additional parameters of the voice query. If it is determined by the search intent algorithms that the information provided by the user or the parameters of the voice query is insufficient for a relevant response to the voice query of the user, the search intent algorithms may follow a predetermined logic tree and ask another question. The questions may be taken from a preloaded list of questions and selected based on the predetermined logic tree. The process of asking additional questions and analyzing the user voice received in response to the additional questions may repeat until the additional information received from the user is sufficient to understand the voice request. When it is determined that enough information is obtained from the user to understand the request, the responses may be scored based on the predetermined criteria using weighting and ranking algorithms. In an example embodiment, the responses may be scored based on the score determined in the course of the analysis of parameters of the voice query and additional parameters determined based on analysis of replies of the user to the additional questions. A response that has a highest rank among the plurality of responses may be provided to the user via the user device or the speaker unit.

Additionally, the method 300 may include determining, based on the voice query, that the user requires assistance of at least one responder. Based on such determination, a request for assistance may be sent to the at least one first responder. The method 300 may further include analyzing the user query based on biosensory data received from sensors and modifying the at least one response based on the analysis. The biosensory data may include at least one of the following: a brain scan, blood pressure, heart rate, body temperature, electrocardiogram, blood oxygenation level, blood sugar level, and so forth.

Figure 4:
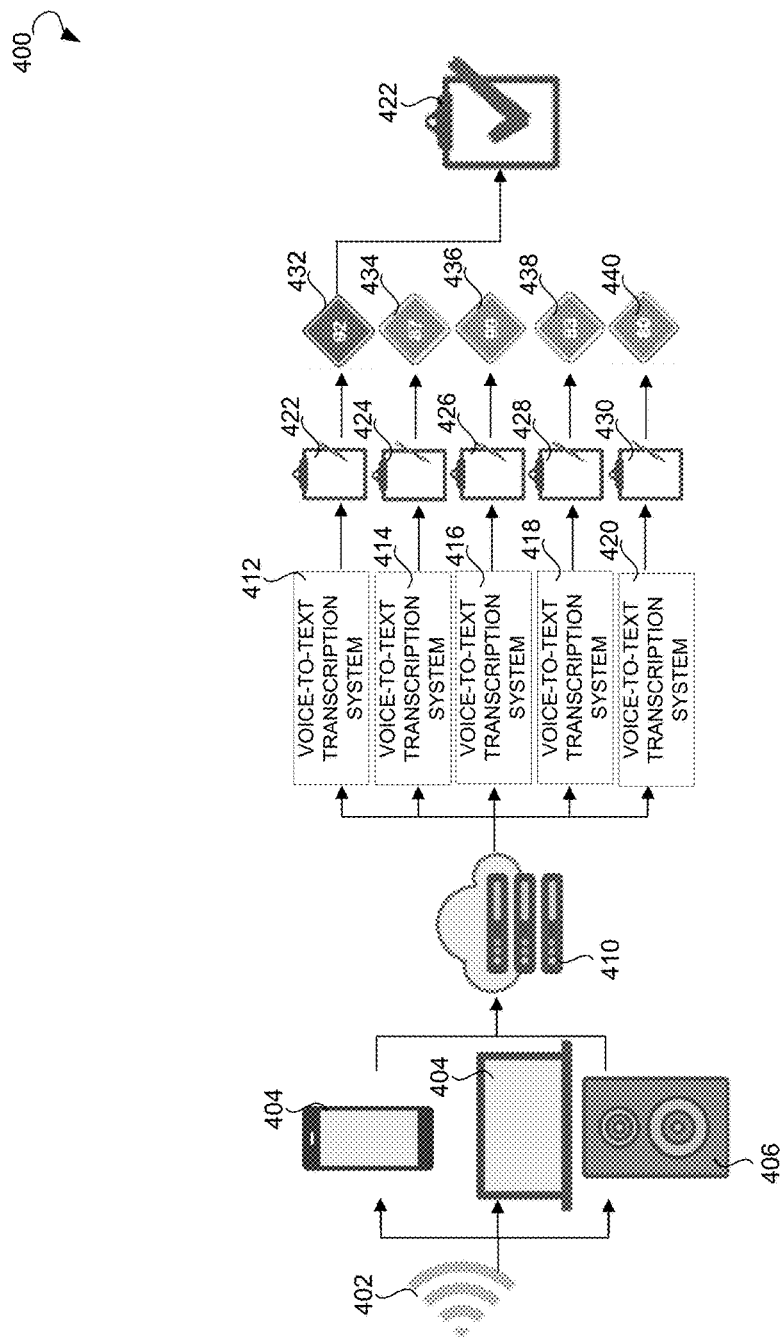
FIG. 4 is a schematic diagram illustrating a method for assisting a voice search of a user, in which a voice query is transmitted to a plurality of voice-to-text transcription systems, in accordance with some example embodiments.

FIG. 4 is a schematic diagram illustrating several example operations of a method 400 for assisting a voice search of a user, in which a voice query is transmitted to a plurality of voice-to-text transcription systems. The user may provide a voice query 402 that is captured by a user device 404 having a microphone or by a speaker unit 406 of any other digital device. Upon being captured, the voice query 402 can be transmitted to a cloud 410 where the voice query 402 is stored. Thereafter, the voice query 402 may be transmitted to a plurality of voice-to-text transcription systems 412, 414, 416, 418, 420. In an example embodiment, any data associated with the voice query 402, such as metadata related to the determined parameters associated with the voice query 402, may be sent to the plurality of voice-to-text transcription systems 412, 414, 416, 418, 420 together with the voice query 402.

Each of the voice-to-text transcription systems 412, 414, 416, 418, 420 may transcribe the voice query 402 into a text query 422, 424, 426, 428, 430. The text query 422, 424, 426, 428, 430 received from each of the voice-to-text transcription systems 412, 414, 416, 418, 420 may be analyzed to determine a score 432, 434, 436, 438, 440 for each of the text queries 422, 424, 426, 428, 430. The analysis may be performed based on predetermined scoring criteria, for example, based on the reliability of each of the voice-to-text transcription systems 412, 414, 416, 418, 420. The reliability may be known or determined based on historic data associated with each of the voice-to-text transcription systems 412, 414, 416, 418, 420. The text queries 422, 424, 426, 428, 430 may be ranked based on the scores 432, 434, 436, 438, 440. Based on the ranking, the text query having the highest rank, e.g., the text query 422, may be selected for further processing.

Figure 5:
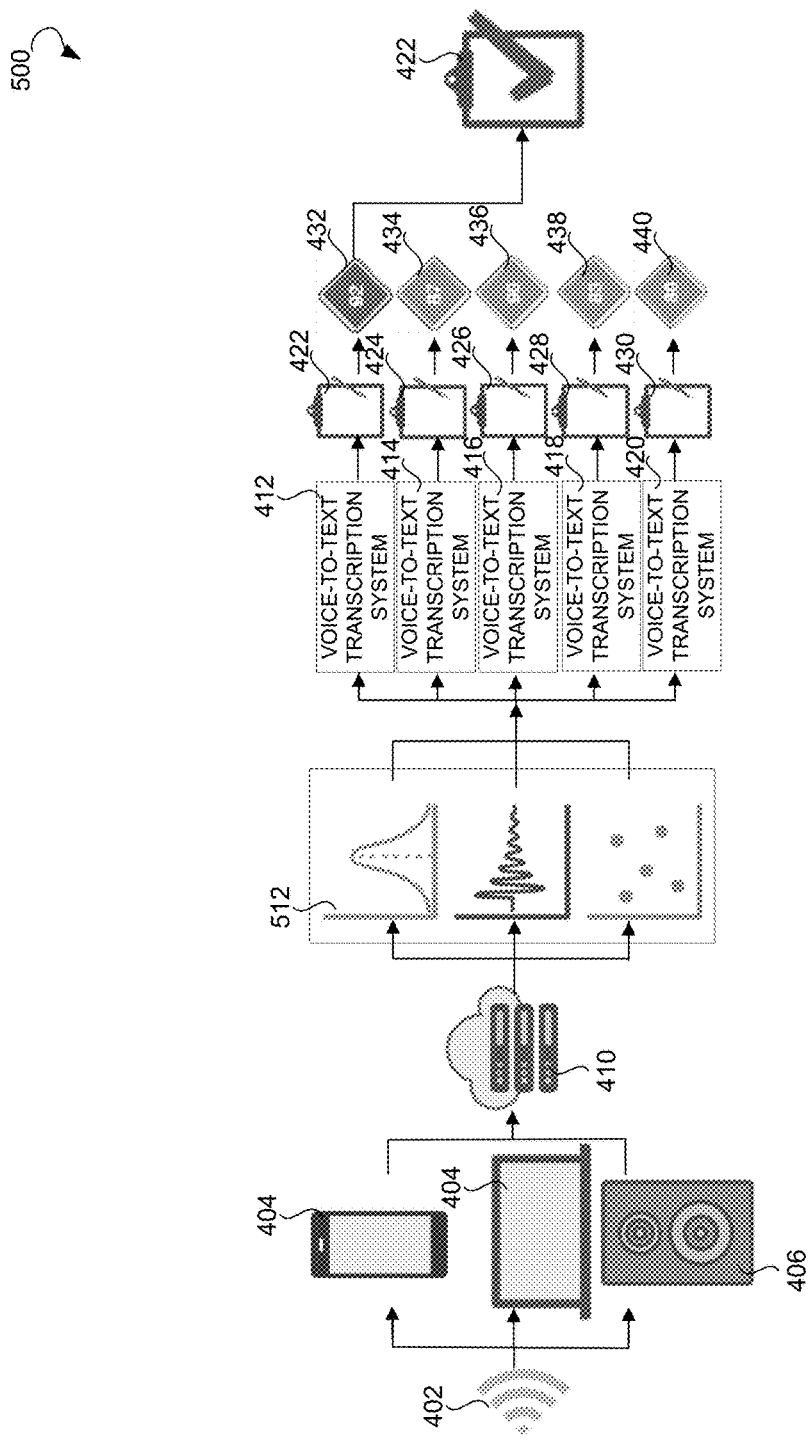
FIG. 5 is a schematic diagram illustrating a method for assisting a voice search of a user, in which a voice query is analyzed using search intent algorithms, according to an example embodiment.

FIG. 5 is a schematic diagram illustrating several operations of a method 500 for assisting a voice search of a user, in which a voice query is analyzed using search intent algorithms, according to an example embodiment. The voice query 402 may be analyzed using search intent algorithms 512 to determine parameters of the voice query 402, such as a tone, tempo, inflection, sentiment, urgency, emphasis of the voice query 402, keyword, term, phrase, content, desire, intent of the voice query, visual cue, gesture, body motion, body language, facial expression associated with the user, environmental parameter, ambient data, user demographics, user location, historical data, and the like. The analysis of the parameters may be used for subsequent scoring of responses generated in response to the voice query 402.

In an example embodiment, additional parameters associated with the voice query 402 can be determined using an image recognition technology. Specifically, the processor of the user device 404 may use the image recognition technology to recognize textual imagery in a proximity of the user as reported by location services of the user device 404. The textual imagery can be captured by a camera associated with the user device 404. The processor of the user device 404 can be configured to activate the camera of the user device 404 and recognize the textual data captured by the camera. The processor can then generate contextual information associated with the recognized textual data. This contextual information can be used in the context of the voice query 402. In an example embodiment, the contextual information can be determined using processing capabilities of the cloud 410. The context may include items captured by the camera, key words, products, names, locations, merchants, and the like.

Figure 6:
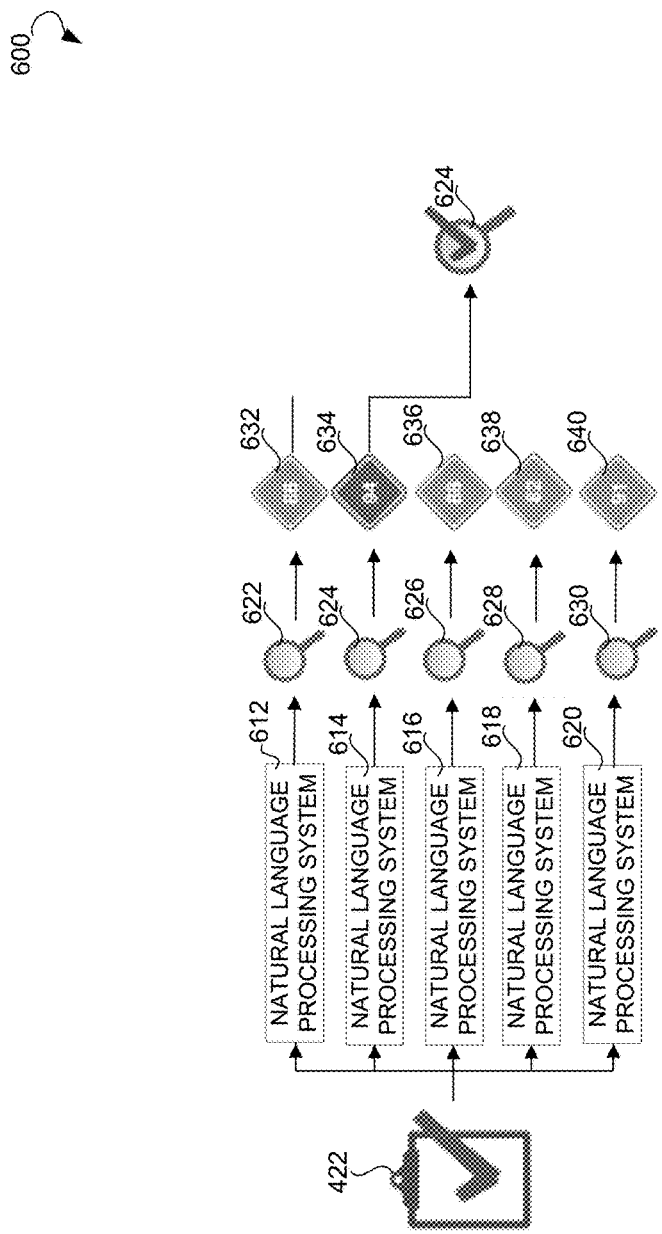
FIG. 6 is a schematic diagram illustrating a method for assisting a voice search of a user, in which a text query is transmitted to a plurality of natural language processing systems, according to an example embodiment.

FIG. 6 is a schematic diagram illustrating several operations of a method 600 for assisting a voice search, in which a text query is transmitted to a plurality of natural language processing systems, according to an example embodiment. The text query 422 selected as described with reference to FIG. 4 can be sent to a plurality of natural language processing systems 612, 614, 616, 618, 620. In an example embodiment, any data associated with the voice query, such as metadata related to the determined parameters associated with the voice query, may be sent to the plurality of natural language processing systems 612, 614, 616, 618, 620 together with the text query 422.

Each of the plurality of natural language processing systems 612, 614, 616, 618, 620 may analyze the text query 422 and provide a result of the analysis, e.g., in a form of search parameter sets 622, 624, 626, 628, 630. The search parameter sets 622, 624, 626, 628, 630 may include key words, terms, phrases, dates, locations, events, brand names, and other content or context parameters.

The search parameter sets 622, 624, 626, 628, 630 received from the natural language processing systems 612, 614, 616, 618, 620 may be analyzed to determine a score 632, 634, 636, 638, 640 for each of the search parameter sets 622, 624, 626, 628, 630. The analysis may be performed based on the predetermined scoring criteria, for example, based on the reliability of each of the natural language processing systems 612, 614, 616, 618, 620. The reliability may be known or determined based on historic data associated with each of the natural language processing systems 612, 614, 616, 618, 620. The search parameter sets 622, 624, 626, 628, 630 may be ranked based on the scores 632, 634, 636, 638, 640. Based on the ranking, the search parameter set having the highest rank, e.g., the search parameter set 624, may be selected for further processing.

Figure 7:
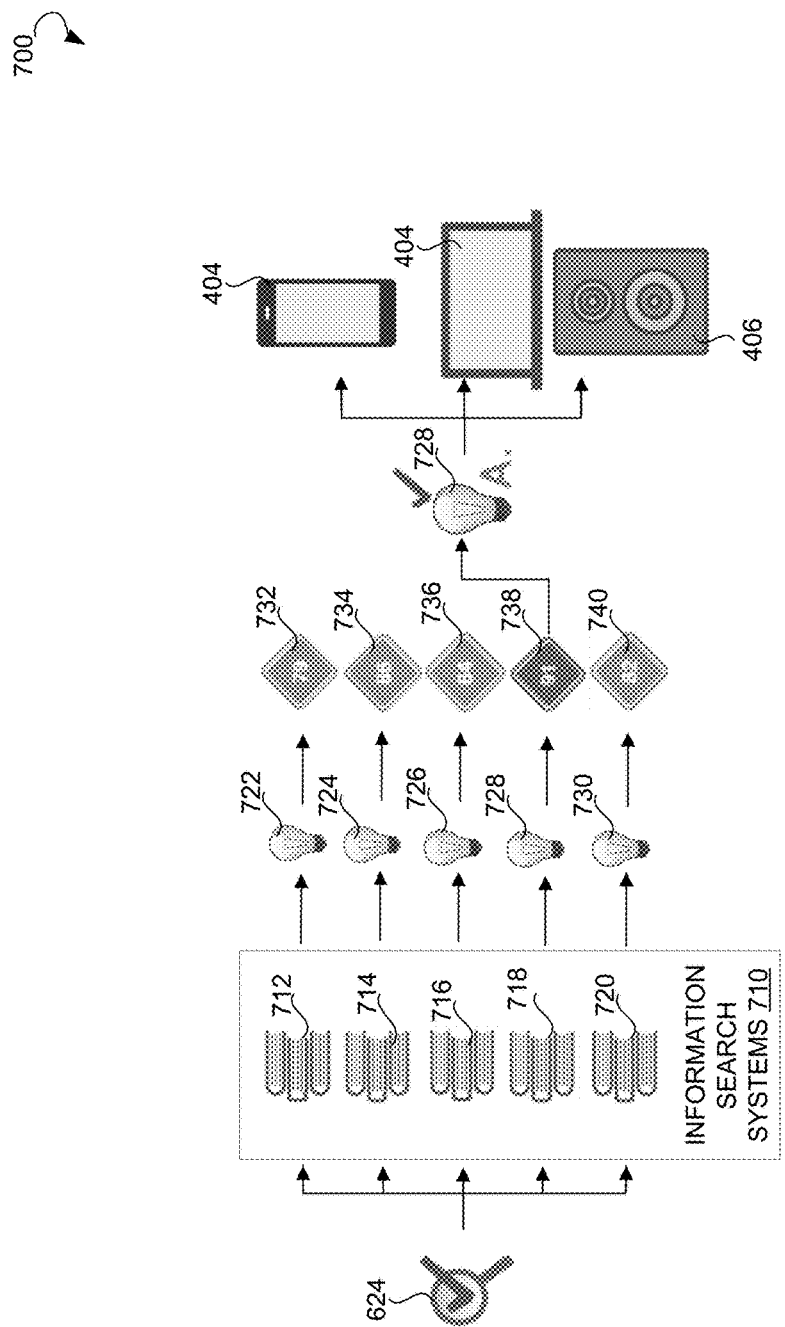
FIG. 7 is a schematic diagram illustrating a method for assisting a voice search of a user, in which a search parameter set is transmitted to a plurality of information search systems including information datasets, according to an example embodiment.

FIG. 7 is a schematic diagram illustrating several operations of a method 700 for assisting a voice search of a user, in which a search parameter set is transmitted to a plurality of information search systems including information datasets, according to an example embodiment. The information search systems may be configured to perform a search based on received input data. The search parameter set 624 selected as described above with reference to FIG. 6 may be sent to a plurality of information search systems 710. The information search systems 710 may include a plurality of information datasets 712, 714, 716, 718, 720. In an example embodiment, the information datasets 712, 714, 716, 718, 720 may include databases for storing data. The information datasets 712, 714, 716, 718, 720 may include topic-specific databases. Each information search system 710 can perform a search based on the search parameter set 624. Based on the search, a plurality of responses 722, 724, 726, 728, 730 may be provided by the information search systems 710.

The responses 722, 724, 726, 728, 730 received from the information search systems 710 can be analyzed to determine a score 732, 734, 736, 738, 740 for each of the responses 722, 724, 726, 728, 730. The analysis may be performed based on the predetermined scoring criteria, for example, based on the reliability of each of the information datasets 712, 714, 716, 718, 720. The reliability may be known or determined based on historic data associated with each of the information datasets 712, 714, 716, 718, 720. The responses 722, 724, 726, 728, 730 may be ranked based on the score 732, 734, 736, 738, 740. The response having the highest rank, e.g., the response 728, may be selected for further presenting to the user via the user device 404 or the speaker unit 406.

Figure 8:
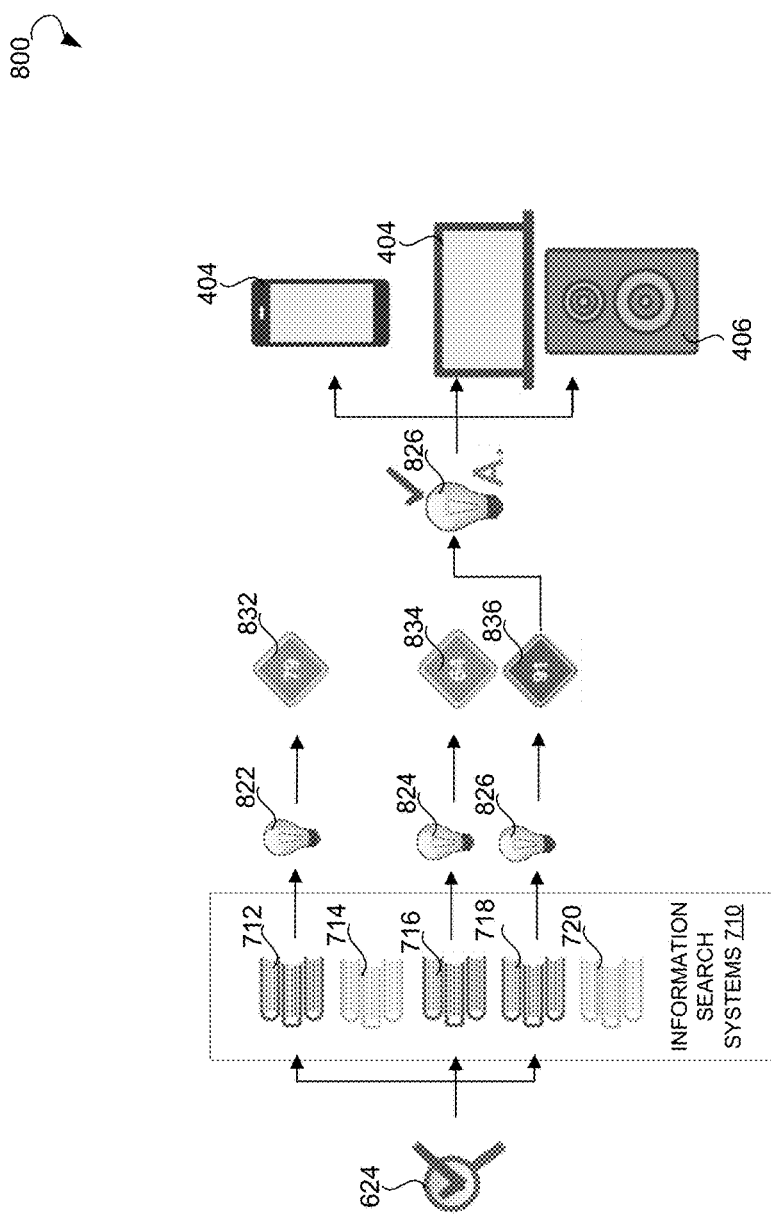
FIG. 8 is a schematic diagram illustrating a method for assisting a voice search of a user, in which a search parameter set is transmitted to selected information search systems, according to an example embodiment.

FIG. 8 is a schematic diagram illustrating several operations of a method 800 for assisting a voice search of a user, in which a search parameter set is transmitted to selected information search systems, according to an example embodiment. In some embodiments, only some of the information datasets 712, 714, 716, 718, 720 are selected for processing the search parameter set 624. The selection of the information datasets applicable for performing the search based on the search parameter set 624 may be made based on historic data associated with the information datasets 712, 714, 716, 718, 720. For example, some of the information datasets 712, 714, 716, 718, 720 may be more reliable or more trusted for processing specific types of data than others.

In a further example embodiments, the natural language processing systems 612, 614, 616, 618, 620 shown in FIG. 6 may provide an indication as to which information datasets 712, 714, 716, 718, 720 can be selected as applicable for processing of one or more of the search parameter sets 622, 624, 626, 628, 630. For example, information datasets 712, 716, 718 can be selected for performing the search based on the search parameter set 624. Based on the search, a plurality of responses 832, 834, 836 can be provided by the information datasets 712, 716, 718.

The responses 832, 834, 836 received from the information datasets 712, 716, 718 may be analyzed to determine a score 832, 834, 836 for each of the responses 822, 824, 826. The analysis may be performed based on the predetermined scoring criteria, for example, based on the reliability of each of the information datasets 712, 716, 718. The reliability may be known or determined based on historic data associated with each of the information datasets 712, 716, 718. The responses 822, 824, 826 may be ranked based on the score 832, 834, 836. Based on the ranking, the response having the highest rank, e.g., the response 826, may be selected for further presenting to the user via the user device 404 or the speaker unit 406.

Figure 9:
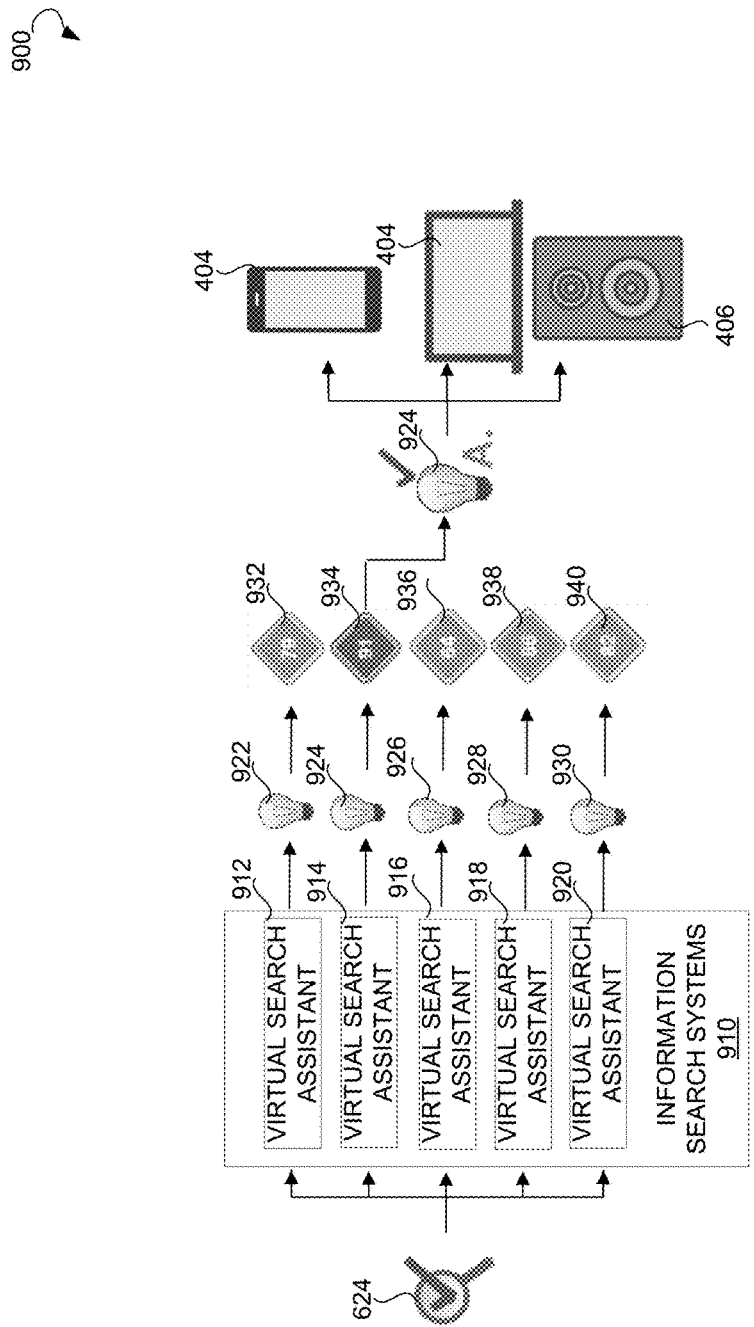
FIG. 9 is a schematic diagram illustrating a method for assisting a voice search of a user, in which a search parameter set is transmitted to information search systems including virtual search assistants, according to an example embodiment.

FIG. 9 is a schematic diagram illustrating several operations of a method 900 for assisting a voice search of a user, in which a search parameter set is transmitted to information search systems including virtual search assistants, according to an example embodiment. The information search systems 910 may be configured to perform a search based on received input data. The search parameter set 624 selected as described with reference to FIG. 6 may be sent to a plurality of information search systems 910. In an example embodiment, any data associated with the voice query, such as metadata related to the determined parameters associated with the voice query, may be sent to the plurality of information search systems 910 together with the search parameter set 624.

The information search systems 910 may include a plurality of virtual search assistants 912, 914, 916, 918, 920. In an example embodiment, the virtual search assistants 912, 914, 916, 918, 920 may include third-party virtual search assistants, such as Google Assistant® from Google, Alexa® from Amazon, Siri® from Apple, Cortana® from Microsoft, Bixby® from Samsung, and so forth. Each of the virtual search assistants 912, 914, 916, 918, 920 may perform a search based on the search parameter set 624. Based on the search, a plurality of responses 922, 924, 926, 928, 930 may be provided by the information search systems 910.

The responses 922, 924, 926, 928, 930 received from the information search systems 910 may be analyzed to determine a score 932, 934, 936, 938, 940 for each of the responses 922, 924, 926, 928, 930. The analysis may be performed based on the predetermined scoring criteria, for example, based on the reliability of each of the virtual search assistants 912, 914, 916, 918, 920. The reliability may be known or determined based on historic data associated with each of the virtual search assistants 912, 914, 916, 918, 920. Furthermore, the responses 922, 924, 926, 928, 930 may be weighted based on a source of search results, i.e. based on the virtual search assistant from which the response was received, so that more reliable search results based on the historical data are assigned higher scores and more relevance. For example, one of the virtual search assistants 912, 914, 916, 918, 920 may be more trusted than the rest of virtual search assistants 912, 914, 916, 918, 920, so the response received from the that virtual assistant may be scored higher or weighted more. The responses 922, 924, 926, 928, 930 may be also weighted based on a sponsorship where any party, e.g., a service provider may pay to be featured at the top of a list of search results. Similarly, a local business may pay for being shown in lists of search results of users that are located in a proximity of the business. The responses 922, 924, 926, 928, 930 may be ranked based on the score 932, 934, 936, 938, 940 and, optionally, based on the weights using weighting and ranking algorithms. Based on the ranking, the response having the highest rank, e.g., the response 924, may be selected for further presenting to the user via the user device 404 or the speaker unit 406.

Figure 10:
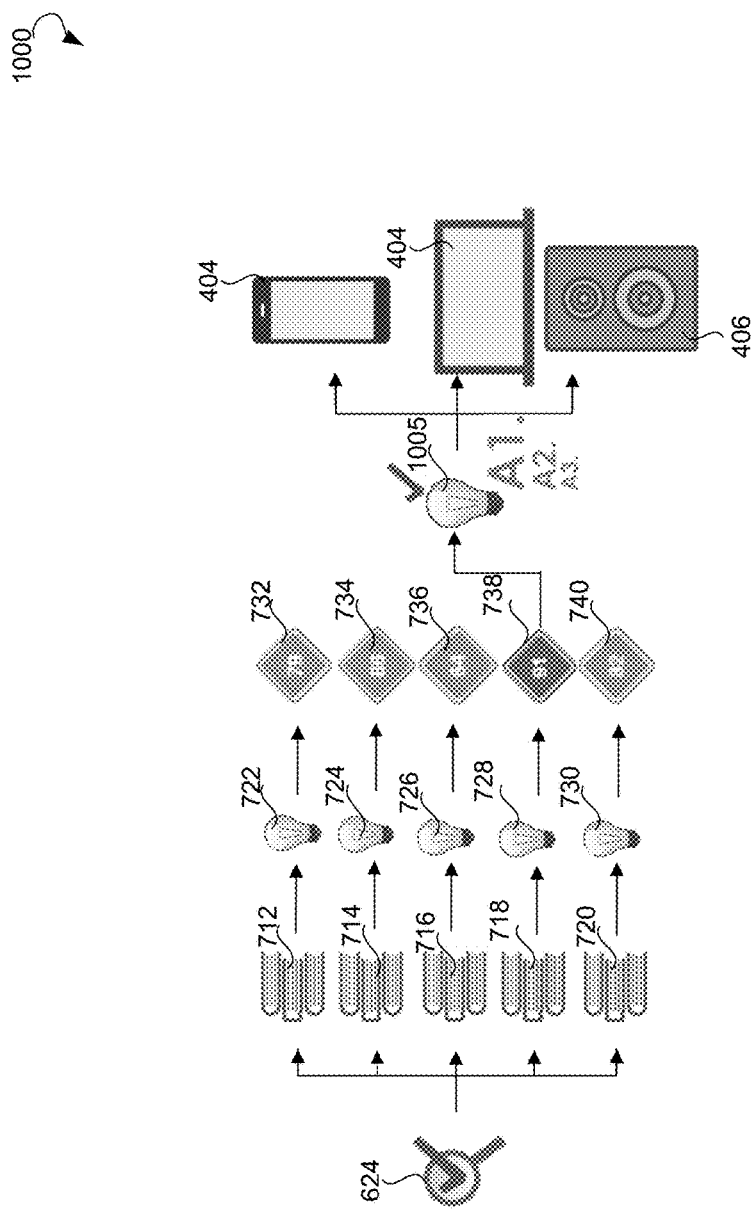
FIG. 10 is a schematic diagram illustrating a method for assisting a voice search of a user, in which a list of ranked responses is provided to a user, according to an example embodiment.

FIG. 10 is a schematic diagram illustrating several operations of a method 1000 for assisting a voice search of a user, in which a list of ranked responses is provided to a user, according to an example embodiment. The search parameter set 624 selected as described with reference to FIG. 6 may be sent to a plurality of information search systems, such as information datasets 712, 714, 716, 718, 720. In an alternative example embodiment, the search parameter set 624 is sent to information search systems including virtual search assistants 912, 914, 916, 918, 920 shown in FIG. 9.

As shown in FIG. 10, each of the information datasets 712, 714, 716, 718, 720 may perform a search based on the search parameter set 624. Based on the search, a plurality of responses 722, 724, 726, 728, 730 may be provided by the information datasets 712, 714, 716, 718, 720. The responses 722, 724, 726, 728, 730 received from the information datasets 712, 714, 716, 718, 720 may be analyzed to determine a score 732, 734, 736, 738, 740 for each of the responses 722, 724, 726, 728, 730. The analysis may be performed based on the predetermined scoring criteria, for example, based on the reliability of each of the information datasets 712, 714, 716, 718, 720. The responses 722, 724, 726, 728, 730 may be ranked based on the score 732, 734, 736, 738, 740. Based on the ranking, a list 1005 of ranked responses may be generated. The list 1005 of ranked responses may be presented to the user via the user device 404 or the speaker unit 406. For example, responses in the list 1005 of ranked responses may be ranked as follows: response 738, response 734, response 740, response 732, and response 736

Figure 11:
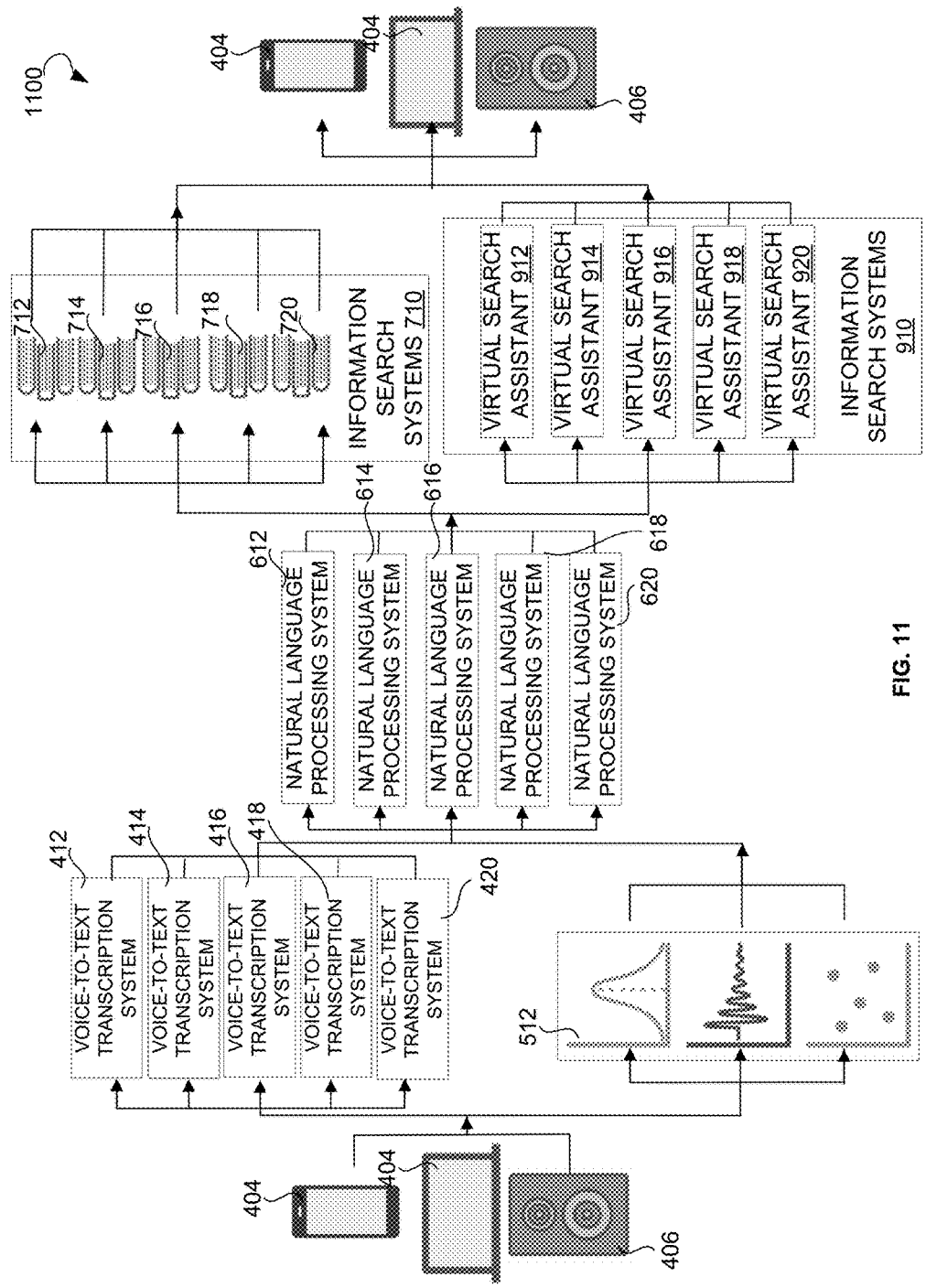
FIG. 11 is a schematic diagram illustrating a method for assisting a voice search of a user and showing a path of processing of a voice query, according to an example embodiment.

FIG. 11 is a schematic diagram illustrating a method 1100 for assisting a voice search of a user and showing a path of processing of a voice query, according to an example embodiment. A voice query provided by a user may be captured by a user device 404 or a speaker unit 406. The user device 404 or the speaker unit 406 may transmit the captured voice query to a plurality of voice-to-text transcription systems 412, 414, 416, 418, 420. In an example embodiment, the voice query may be analyzed using search intent algorithms 512 to determine parameters associated with the voice query.

The plurality of voice-to-text transcription systems 412, 414, 416, 418, 420 may process the voice query and provide a plurality of text queries. At least one text query may be selected from the plurality of text queries and sent to a plurality of natural language processing systems 612, 614, 616, 618, 620. The plurality of natural language processing systems 612, 614, 616, 618, 620 may process the at least one text query and provide a plurality of search parameter sets.

At least one search parameter set may be selected from the plurality of search parameter sets and sent to one of information search systems 710 or 910. The information search systems 710 may include a plurality of information datasets 712, 714, 716, 718, 720. The information search systems 910 may include a plurality of virtual search assistants 912, 914, 916, 918, 920. In an example embodiment, the least one search parameter set is sent to both the plurality of information datasets 712, 714, 716, 718, 720 and the plurality of virtual search assistants 912, 914, 916, 918, 920. The plurality of information datasets 712, 714, 716, 718, 720 or the plurality of virtual search assistants 912, 914, 916, 918, 920 may provide a plurality of responses to the voice query. The plurality of responses may be generated based on the search performed by the plurality of information datasets 712, 714, 716, 718, 720 or the plurality of virtual search assistants 912, 914, 916, 918, 920 using the at least one search parameter set. At least one response may be selected from the plurality of responses and provided to the user device 404 or the speaker unit 406 associated with the user.

Figure 12:
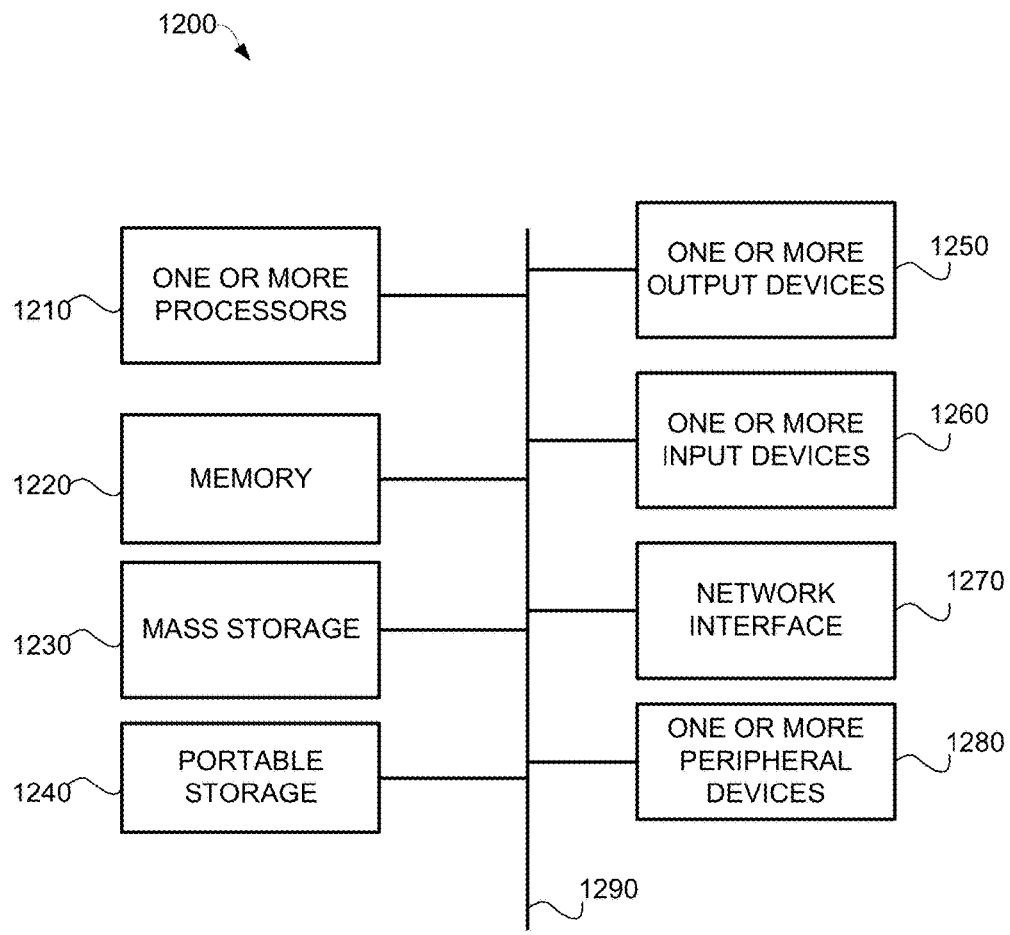
FIG. 12 shows a computing system that can be used to implement a method for assisting voice searches, according to an example embodiment.

FIG. 12 illustrates an exemplary computing system 1200 that may be used to implement embodiments described herein. The exemplary computing system 1200 of FIG. 12 may include one or more processors 1210 and memory 1220. Memory 1220 may store, in part, instructions and data for execution by the one or more processors 1210. Memory 1220 can store the executable code when the exemplary computing system 1200 is in operation. The exemplary computing system 1200 of FIG. 12 may further include a storage 1230, portable storage 1240, one or more output devices 1250, one or more input devices 1260, a network interface 1270, and one or more peripheral devices 1280.

The components shown in FIG. 12 are depicted as being connected via a single bus 1290 solely for the purposes of illustration. The components may be connected through one or more data transport means. In some example embodiments, components shown in FIG. 12 are virtual and/or implemented as cloud-based distributed resources.

Storage 1230, which may be implemented with a magnetic disk drive, an optical disk drive, or a solid-state drive is a non-volatile storage device for storing data and instructions for use by the magnetic disk, optical disk drive, or solid-state drive which in turn may be used by one or more processors 1210. Storage 1230 can store the system software for implementing embodiments described herein for purposes of loading that software into memory 1220.

Portable storage 1240 may operate in conjunction with a portable non-volatile storage medium, such as a compact disk (CD), or digital video disc (DVD), flash drive to input and output data and code to and from the computing system 1200 of FIG. 12. The system software for implementing embodiments described herein may be stored on such a portable medium and input to the computing system 1200 via the portable storage 1240.

One or more input devices 1260 provide a portion of a user interface. The one or more input devices 1260 may include an alphanumeric keypad, such as a keyboard, for inputting alphanumeric and other information, or a pointing device, such as a mouse, a trackball, a stylus, or cursor direction keys. Additionally, the computing system 1200 as shown in FIG. 12 includes one or more output devices 1250. Suitable one or more output devices 1250 include speakers, printers, network interfaces, and monitors.

Network interface 1270 can be utilized to communicate with external devices, external computing devices, servers, and networked systems via one or more communications networks such as one or more wired, wireless, or optical networks including, for example, the Internet, intranet, LAN, WAN, cellular phone networks (e.g., Global System for Mobile communications network, packet switching communications network, circuit switching communications network), Bluetooth radio, and an IEEE 802.11-based radio frequency network, among others. Network interface 1270 may be a network interface card, such as an Ethernet card, optical transceiver, radio frequency transceiver, or any other type of device that can send and receive information. Other examples of such network interfaces may include Bluetooth®, 3G, 4G, and WiFi® radios in mobile computing devices as well as a USB.

One or more peripheral devices 1280 may include any type of computer support device to add additional functionality to the computing system. The one or more peripheral devices 1280 may include a modem or a router.

The components contained in the exemplary computing system 1200 of FIG. 12 are those typically found in computing systems that may be suitable for use with embodiments described herein and are intended to represent a broad category of such computer components that are well known in the art. Thus, the exemplary computing system 1200 of FIG. 12 can be a personal computer, hand held computing device, telephone, mobile computing device, workstation, server, minicomputer, mainframe computer, or any other computing device. The computer can also include different bus configurations, networked platforms, multi-processor platforms, and so forth. Various operating systems (OS) can be used including UNIX, Linux, Windows, Macintosh OS, Palm OS, and other suitable operating systems.

Some of the above-described functions may be composed of instructions that are stored on storage media (e.g., computer-readable medium). The instructions may be retrieved and executed by the processor. Some examples of storage media are memory devices, tapes, disks, and the like. The instructions are operational when executed by the processor to direct the processor to operate in accord with the example embodiments. Those skilled in the art are familiar with instructions, processor(s), and storage media.

It is noteworthy that any hardware platform suitable for performing the processing described herein is suitable for use with the example embodiments. The terms "computer-readable storage medium" and "computer-readable storage media" as used herein refer to any medium or media that participate in providing instructions to a CPU for execution. Such media can take many forms, including, but not limited to, non-volatile media, volatile media, and transmission media. Non-volatile media include, for example, optical or magnetic disks, such as a fixed disk. Volatile media include dynamic memory, such as RAM. Transmission media include coaxial cables, copper wire, and fiber optics, among others, including the wires that include one embodiment of a bus. Transmission media can also take the form of acoustic or light waves, such as those generated during radio frequency and infrared data communications. Common forms of computer-readable media include, for example, a floppy disk, a flexible disk, a hard disk, magnetic tape, any other magnetic medium, a CD-read-only memory (ROM) disk, DVD, any other optical medium, any other physical medium with patterns of marks or holes, a RAM, a PROM, an EPROM, an EEPROM, a FLASHEPROM, any other memory chip or cartridge, a carrier wave, or any other medium from which a computer can read.

Various forms of computer-readable media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU.

Thus, systems and methods for assisting voice searches are described. Although embodiments have been described with reference to specific exemplary embodiments, it will be evident that various modifications and changes can be made to these exemplary embodiments without departing from the broader spirit and scope of the present application. Accordingly, the specification and drawings are to be regarded in an illustrative rather than a restrictive sense.

What is claimed is:

1. A system for assisting voice searches, the system comprising:
    a processor configured to:
        receive a voice query from a user;
        transmit the voice query to a plurality of natural language processing systems;
        receive a plurality of search parameter sets from the plurality of natural language processing systems, the plurality of search parameter sets being generated by the plurality of natural language processing systems based on the voice query;
        transmit at least one of the plurality of search parameter sets to a plurality of information search systems;
        receive a plurality of responses from the plurality of information search systems, the plurality of responses being generated by the plurality of information search systems based on the at least one of the plurality of search parameter sets;
        score each of the plurality of responses based on predetermined scoring criteria;
        rank the plurality of responses based on the score to select at least one response of the plurality of responses;
        assign weights to each of the plurality of responses based on the score; and
        provide the at least one response of the plurality of responses to the user, wherein the at least one response is a combination of the plurality of responses received from the plurality of information search systems based on the assigned weights; and
    a database communicatively coupled to the processor, the database storing instructions executable by the processor.

2. The system of claim 1, wherein the processor is further configured to:
    score each of the plurality of search parameter sets based on the predetermined scoring criteria; and
    rank the plurality of search parameter sets based on the scoring to select the at least one of the plurality of search parameter sets, the at least one of the plurality of search parameter sets having a highest rank.

3. The system of claim 1, wherein the predetermined scoring criteria include at least one of the following: environmental sensor data, user demographics, key word assessment based on a user location, historical data indicative of general reliability of the plurality of the natural language processing systems, historical data indicative of reliability of the plurality of the information search systems with respect to the voice query, historical data indicative of general reliability of the plurality of the voice-to-text transcription systems, and historical data indicative of general reliability of the plurality of the information search systems.

4. The system of claim 1, wherein the processor is further configured to analyze parameters associated with the voice query, wherein the scoring of each of the plurality of responses is further based on the parameters associated with the voice query, wherein the analyzing the parameters associated with the voice query includes using at least one of artificial intelligence and machine learning techniques.

5. The system of claim 4, wherein the parameters include at least one of the following: a tone, a tempo, an inflection, a sentiment, an urgency, an emphasis, a keyword, a term, a phrase, a visual cue, a gesture, a body motion, a body language, a desire, an intent, a facial expression, an environmental parameter, ambient data, user demographics, a user location, historical data, and textual data associated with a location of the user captured using image recognition technology.

6. The system of claim 5, wherein the sentiment, the inflection, the tone, the urgency, the desire, and the intent are determined using search intent algorithms, wherein the visual cue is obtained via a camera and includes at least one of a background and a landmark.

7. The system of claim 1, wherein the plurality of information search systems include at least one of the following: a plurality of information datasets and a plurality of virtual search assistants.

8. The system of claim 1, wherein the transmitting of the voice query to the plurality of natural language processing systems includes:
transmitting the voice query to a plurality of voice-to-text transcription systems;
receiving a plurality of text queries from the plurality of voice-to-text transcription systems; and
sending at least one of the plurality of text queries to the plurality of natural language processing systems,
wherein the plurality of natural language processing systems process the voice query by processing the at least one of the plurality of text queries.

9. The system of claim 8, further comprising:
scoring each of the plurality of text queries based on the predetermined scoring criteria; and
based on the score, selecting the at least one of the plurality of text queries, the at least one of the plurality of text queries having a highest score.

10. The system of claim 1, wherein the plurality of search parameter sets include one or more of the following: key words, terms, phrases, dates, locations, events, and brand names.

11. A method for assisting voice searches, the method comprising:
receiving, by a processor, a voice query from a user;
transmitting, by the processor, the voice query to a plurality of natural language processing systems;
receiving, by the processor, a plurality of search parameter sets from the plurality of natural language processing systems, the plurality of search parameter sets being generated by the plurality of natural language processing systems based on the voice query;
transmitting, by the processor, at least one of the plurality of search parameter sets to a plurality of information search systems;
receiving, by the processor, a plurality of responses from the plurality of information search systems, the plurality of responses being generated by the plurality of information search systems based on the at least one of the plurality of search parameter sets;
scoring, by the processor, each of the plurality of responses based on predetermined scoring criteria;
ranking, by the processor, the plurality of responses based on the score to select at least one response of the plurality of responses;
assigning, by the processor, weights to each of the plurality of responses based on the score; and
providing, by the processor, the at least one response of the plurality of responses to the user, wherein the at least one response is a combination of the plurality of responses received from the plurality of information search systems based on the assigned weights.

12. The method of claim 11, further comprising:
determining, based on the voice query, that more information is needed to clarify the voice query; and
based on the determination, generating at least one follow-up question to clarify the voice query.

13. The method of claim 11, further comprising:
determining, based on the voice query, that the user requires help of at least one first responder; and
based on the determination, sending a request for help to the at least one first responder.

14. The method of claim 11, further comprising:
analyzing the voice query based on biosensory data received from sensors, wherein the biosensory data includes at least one of the following: a brain scan, a blood pressure, a heart rate, a body temperature, an electrocardiogram, a blood oxygenation level, and a blood sugar level; and
modifying the at least one response based on the analysis.

15. The method of claim 11, further comprising ranking the plurality of responses based on sponsored recommendations and/or suggestions related to context of the voice query and/or based on context of historical actions performed by the user.

16. The method of claim 11, further comprising:
selecting and adding, by an Augmented Reality (AR) means, items to an environment to generate an augmented environment; and
showing, by the AR means, the augmented environment to the user in combination with the at least one response.

17. A system for assisting voice searches, the system comprising:
a processor configured to:
receive a voice query from a user;
transmit the voice query to a plurality of natural language processing systems, wherein the transmitting of the voice query to the plurality of natural language processing systems includes:
transmitting the voice query to a plurality of voice-to-text transcription systems;
receiving a plurality of text queries from the plurality of voice-to-text transcription systems;
scoring each of the plurality of text queries based on predetermined scoring criteria;
based on the score, selecting at least one of the plurality of text queries, the at least one of the plurality of text queries having a highest score; and
sending the at least one of the plurality of text queries to the plurality of natural language processing systems, wherein the plurality of natural language processing systems process the voice query by processing of the at least one of the plurality of text queries;
receive a plurality of search parameter sets from the plurality of natural language processing systems, the plurality of search parameter sets being generated by the plurality of natural language processing systems based on the voice query;

score each of the plurality of search parameter sets based on the predetermined scoring criteria;
rank the plurality of search parameter sets based on the scoring to select at least one of the plurality of search parameter sets, the at least one of the plurality of search parameter sets having a highest rank;
transmit the at least one of the plurality of search parameter sets to a plurality of information search systems;
receive a plurality of responses from the plurality of information search systems, the plurality of responses being generated by the plurality of information search systems based on the at least one of the plurality of search parameter sets;
score each of the plurality of responses based on the predetermined scoring criteria;
rank the plurality of responses based on the score to select at least one response of the plurality of responses;
assign weights to each of the plurality of responses based on the score; and
provide the at least one response of the plurality of responses to the user, wherein the at least one response is a combination of the plurality of responses received from the plurality of information search systems based on the assigned weights; and
a database communicatively coupled to the processor, the database storing instructions executable by the processor.

* * * * *